United States Patent [19]

Trenkle et al.

[11] 4,202,994
[45] May 13, 1980

[54] SUBSTITUTED 1-OXYALKYL-2,6,6-TRIMETHYL-CYCLOHEXENE DERIVATIVES, ORGANOLEPTIC USES THEREOF, SYNTHESES FOR PREPARING SAME AND INTERMEDIATES USED IN SAID SYNTHESES

[75] Inventors: Robert W. Trenkle, Bricktown; Braja D. Mookherjee, Holmdel; Robin L. Kasper, Eatontown; Manfred H. Vock, Locust, all of N.J.

[73] Assignee: International Flavors & Fragrances Inc., New York, N.Y.

[21] Appl. No.: 3,905

[22] Filed: Jan. 16, 1979

[51] Int. Cl.$^2$ .............................................. C07F 3/02
[52] U.S. Cl. .................................... 568/824; 568/378
[58] Field of Search ...................... 260/586 R; 568/824

[56] References Cited

U.S. PATENT DOCUMENTS

| | | | |
|---|---|---|---|
| 3,899,597 | 8/1975 | Mookherjee et al. | 568/824 |
| 3,928,248 | 12/1975 | Mookherjee et al. | 260/586 R |
| 3,931,326 | 1/1976 | Kovats et al. | 260/586 R |
| 3,932,485 | 1/1976 | Surmatis | 568/824 |
| 4,054,606 | 10/1977 | Naf | 260/586 R |

*Primary Examiner*—Norman Morgenstern
*Attorney, Agent, or Firm*—Arthur L. Liberman; Franklin D. Wolffe

[57] ABSTRACT

Described are substituted 1-oxyalkyl-2,6,6-trimethylcyclohexene derivatives having the generic structure:

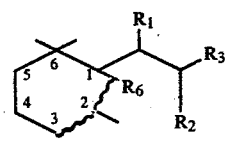

wherein $R_1$ is one of OH,

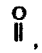

OMgX or H; $R_2$ is

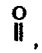

OH, OMgX, CH$_3$, H; $R_3$ is one of methyl, ethyl, 1-propyl or 2-propyl; X is chloro, bromo or iodo; $R_6$ is hydrogen or no moiety; one of the wavy lines is a carbon-carbon double and the other of the wavy lines is a carbon-carbon single bond; with the first proviso that when the $\Delta^{2,3}$ bond is a carbon-carbon double bond, then $R_6$ is hydrogen and the moieties $R_6$ and

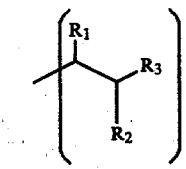

are so juxtaposed as to give rise to two different groups of stereoisomers of the molecular genus:

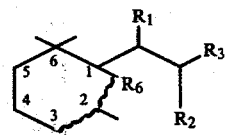

and with the second proviso that when $R_1$ is one of

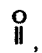

OH or OMgX then $R_2$ is hydrogen or methyl; and when $R_2$ is one of $\overset{O}{\underset{\|}{}}$ OH or OMgX then $R_1$ is hydrogen. Also described are processes for preparing such 1-oxyalkyl-2,6,6-trimethyl cyclohexene derivatives and organoleptic uses of such 1-oxyalkyl-2,6,6-trimethyl cyclohexene derivatives, with the exception of compounds wherein one of $R_1$ or $R_2$ is OMgX.

3 Claims, 6 Drawing Figures

NMR SPECTRUM FOR EXAMPLE I.

IR SPECTRUM FOR EXAMPLE II.

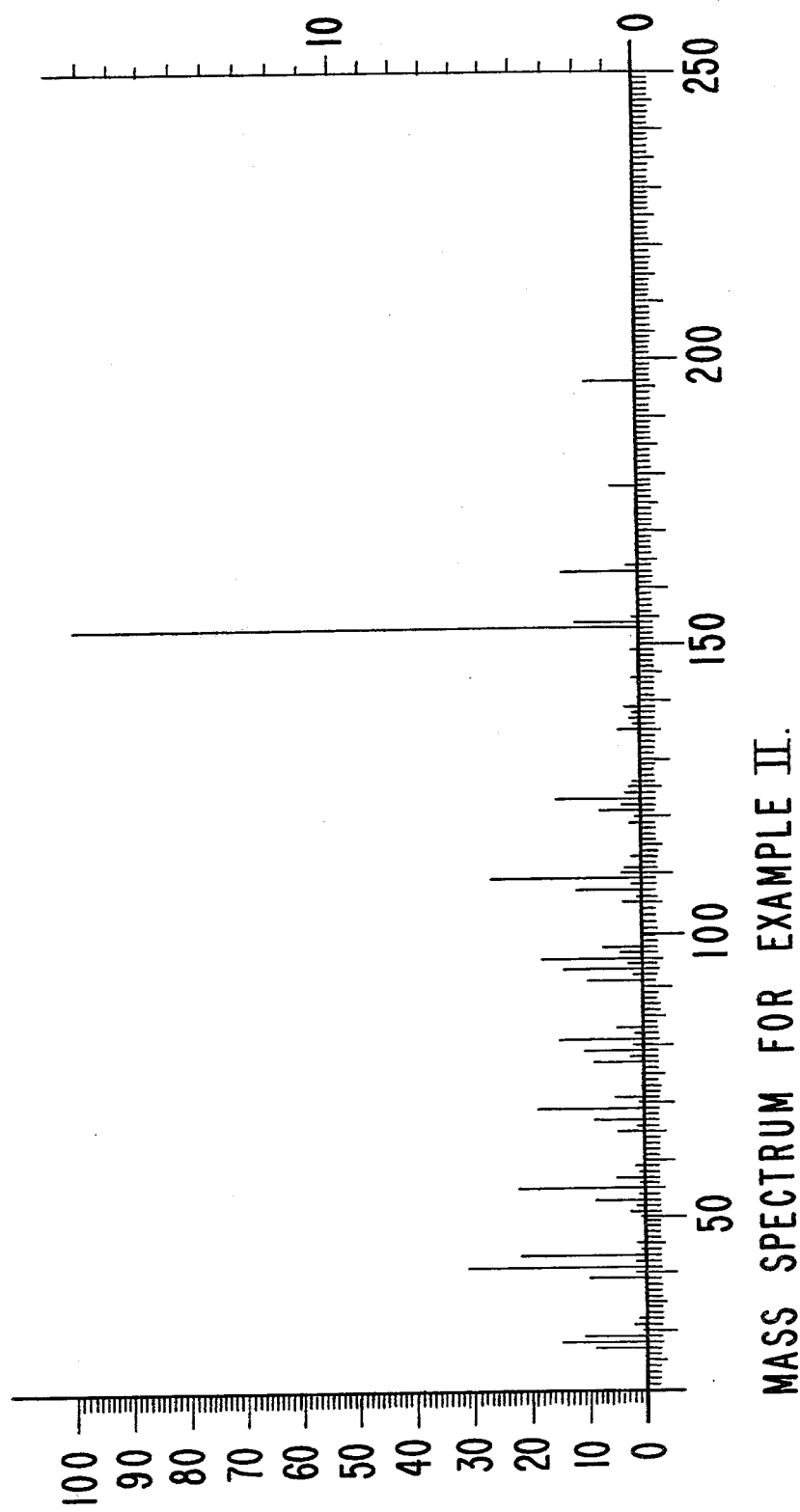
FIG.5 MASS SPECTRUM FOR EXAMPLE II.

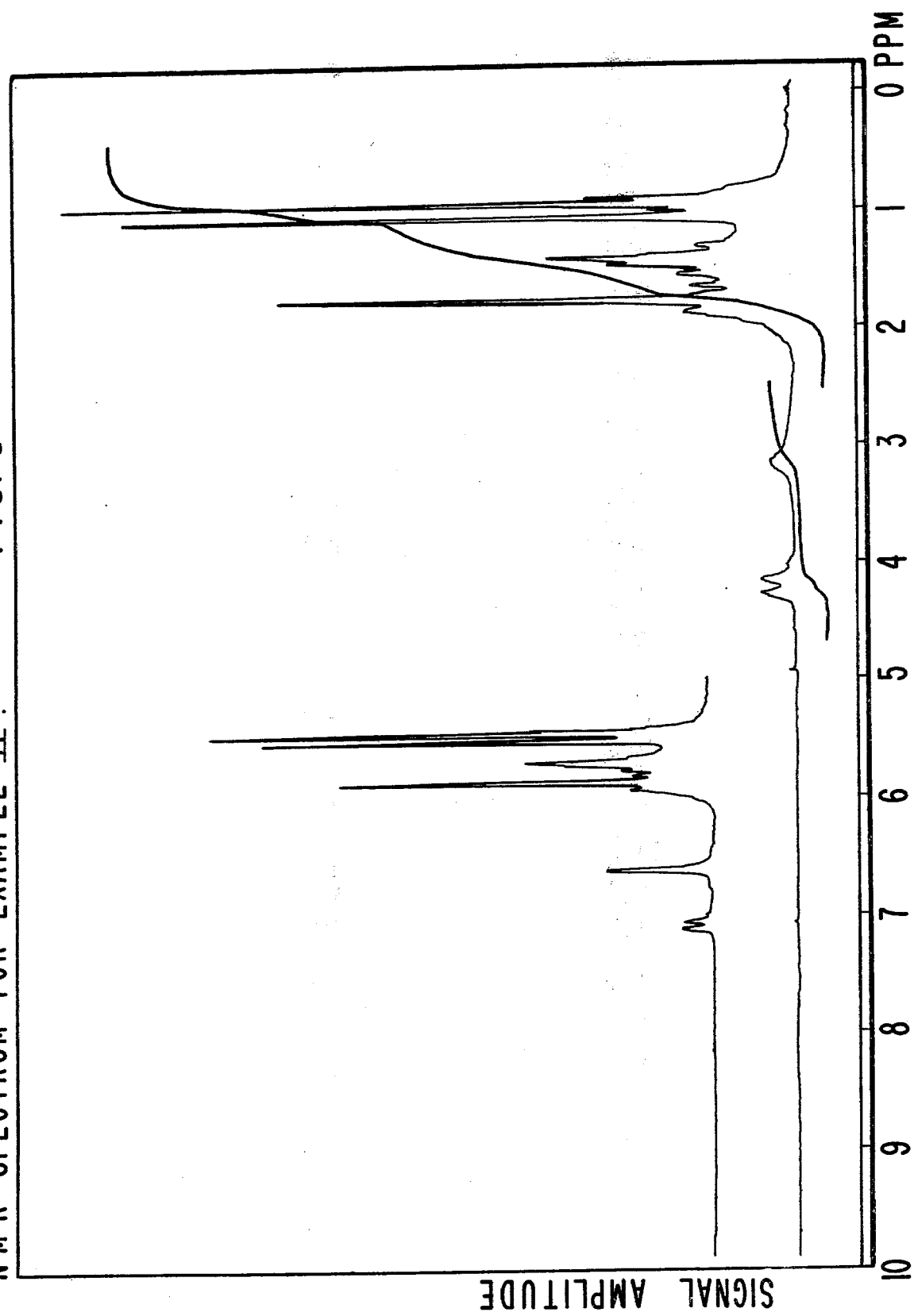

SUBSTITUTED 1-OXYALKYL-2,6,6-TRIMETHYL-CYCLOHEXENE DERIVATIVES, ORGANOLEPTIC USES THEREOF, SYNTHESES FOR PREPARING SAME AND INTERMEDIATES USED IN SAID SYNTHESES

BACKGROUND OF THE INVENTION

The present invention relates to 1-oxyalkyl-2,6,6-trimethylcyclohexene derivatives defined by the generic structure:

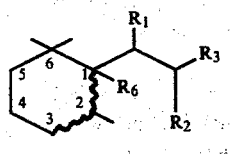

wherein $R_1$ is one of OH,

OMgX or H; $R_2$ is

OH, OMgX, CH$_3$, H; $R_3$ is one of methyl, ethyl, 1-propyl or 2-propyl; X is chloro, bromo or iodo; $R_6$ is hydrogen or no moiety; one of the wavy lines is a carbon-carbon double and the other of the wavy lines is a carbon-carbon single bond; with the first proviso that when the $\Delta^{2,3}$ bond is a carbon-carbon double bond, then $R_6$ is hydrogen and the moieties $R_6$ and

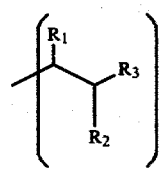

are so juxtaposed as to give rise to two different groups of stereoisomers of the molecular genus:

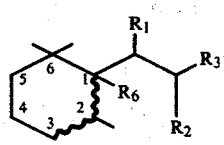

and with the second proviso that when $R_1$ is one of

OH or OMgX then $R_2$ is hydrogen or methyl; and when $R_2$ is one of

O
‖ ,

OH or OMgX then $R_1$ is hydrogen.

These compounds are prepared by straightforward economical process also covered by this invention. Said process is illustrated by the following reaction sequence:

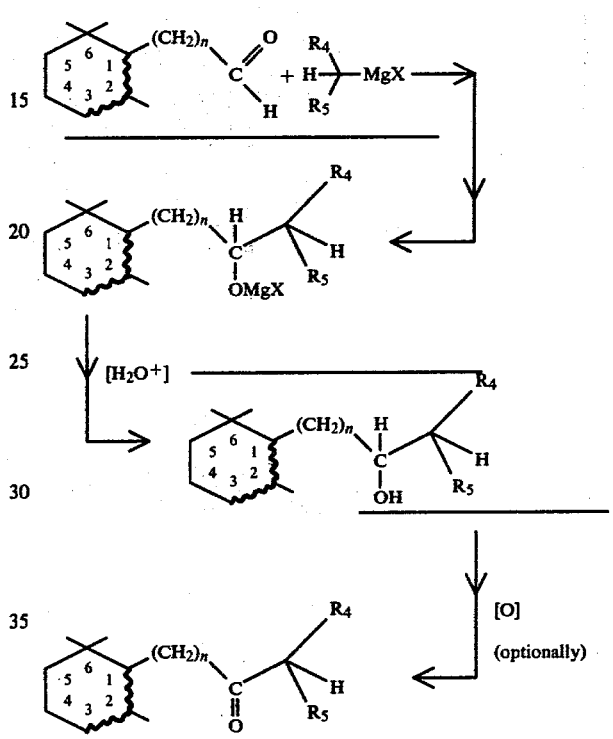

wherein $R_4$ and $R_5$ are each the same or different and each represents hydrogen, methyl or ethyl and the sum, "s" of carbon atoms in $R_4$ and $R_5$ taken together is governed by the mathematical inequality $1 \leq S \leq 2$.

The present invention also provides for the utilization of several compounds produced by our invention and several mixtures produced by the process of our invention for augmenting or enhancing the aroma or taste of foodstuffs, foodstuff flavoring compositions, chewing gums and medicinal products.

There is a continuing search for foodflavor compositions which can vary, fortify, modify, enhance, augment or otherwise improve the flavor and/or aroma of foodstuffs, medicinal products, toothpastes and chewing gum. To be satisfactory, such compositions should be stable, non-toxic and blendable with other ingredients to provide their own unique flavor and aroma nuances without detracting from the contributions of the co-ingredients. Preferably, such compositions should be naturally occurring or present in natural foodstuffs so that their ingestible safety can be readily recognized. These materials should be capable of being synthesized in a simple and economical manner. The need for safe flavors in the berry fruit flavor area, especially the raspberry area, the blueberry flavor area and the apple flavor area is well known particularly in the fruit juice, ice cream and yogurt flavor areas. In addition, there is a need for the development of non-toxic materials which can replace natural materials not readily available having camphoraceous, herbaceous, minty, musty/earthy, oriental, floral/oriental, fruity, raspberry-like, sweet, peach-like, woody, damascenone-like and tobacco like aroma and flavor characteristics.

Such aroma and taste nuances are particularly useful in the raspberry flavor, peach flavor, dried fruit flavor, apple flavor, blueberry flavor, nut flavor, peppermint flavor and tobacco like flavor containing foodstuffs.

The instant invention provides the foregoing which the prior art has heretofore failed to provide. Furthermore, nothing in the prior art shows the unexpected, unobvious and advantageous value of carrying out reaction of an alkyl Grignard reagent with betacyclocitral, alphacyclocitral, betahomocyclocitral or alphahomocyclocitral which compounds are themselves known for their organoleptic uses and which are readily and economically available.

Swiss Pat. No. 557,422 discloses for use in perfumery compounds having the structures:

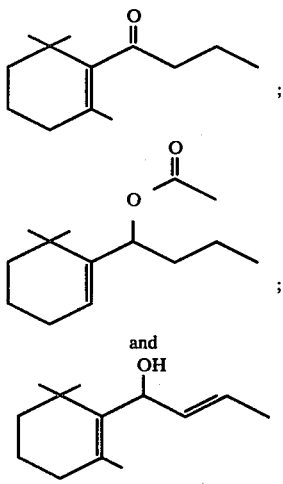

and

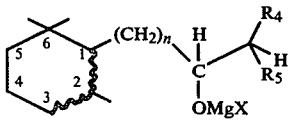

Nothing in the prior art however, discloses the flavor use of the compounds disclosed in the instant specification and furthermore, nothing in the prior art discloses the organometalic compounds of our invention having the generic structure:

wherein one of the wavy lines is a carbon-carbon double bond and the other of the wavy lines is a carbon-carbon single bond; wherein n is zero or 1; wherein X is chloro, bromo or iodo; and wherein $R_4$ and $R_5$ are each the same or different and each represents hydrogen, methyl or ethyl; and wherein the sum, "s," of carbon atoms in $R_4$ and $R_5$ taken together as governed by the mathematical inequality $1 \leq S \leq 2$.

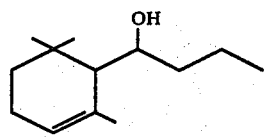

Figure 2:
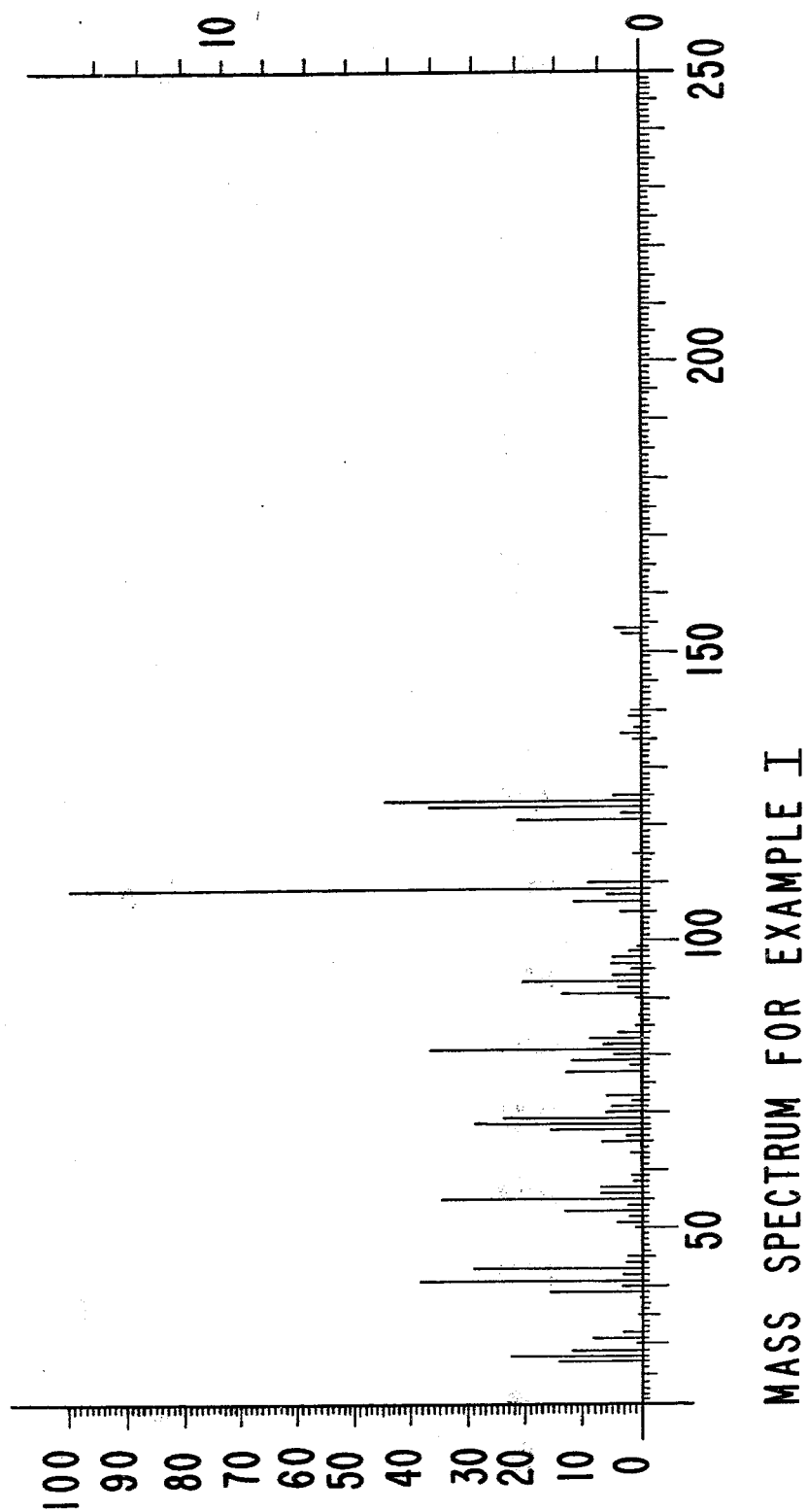

FIG. 2 sets forth the mass spectrum for the compound having the structure:

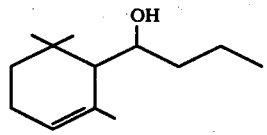

produced according to Example I.

Figure 3:
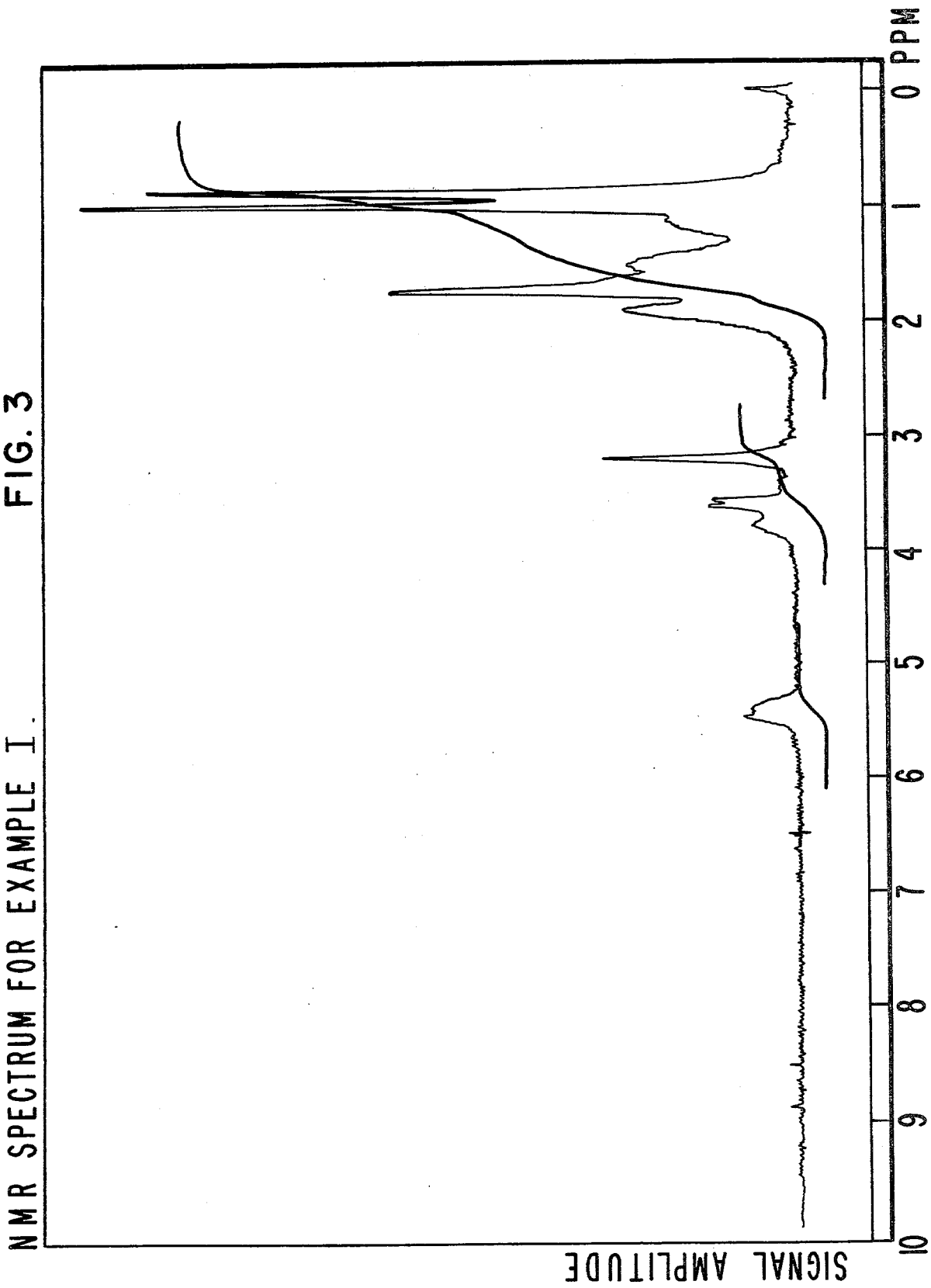

FIG. 3 sets forth the NMR spectrum for the compound having the structure:

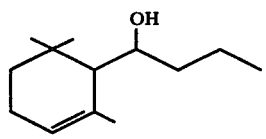

produced according to Example I.

Figure 4:
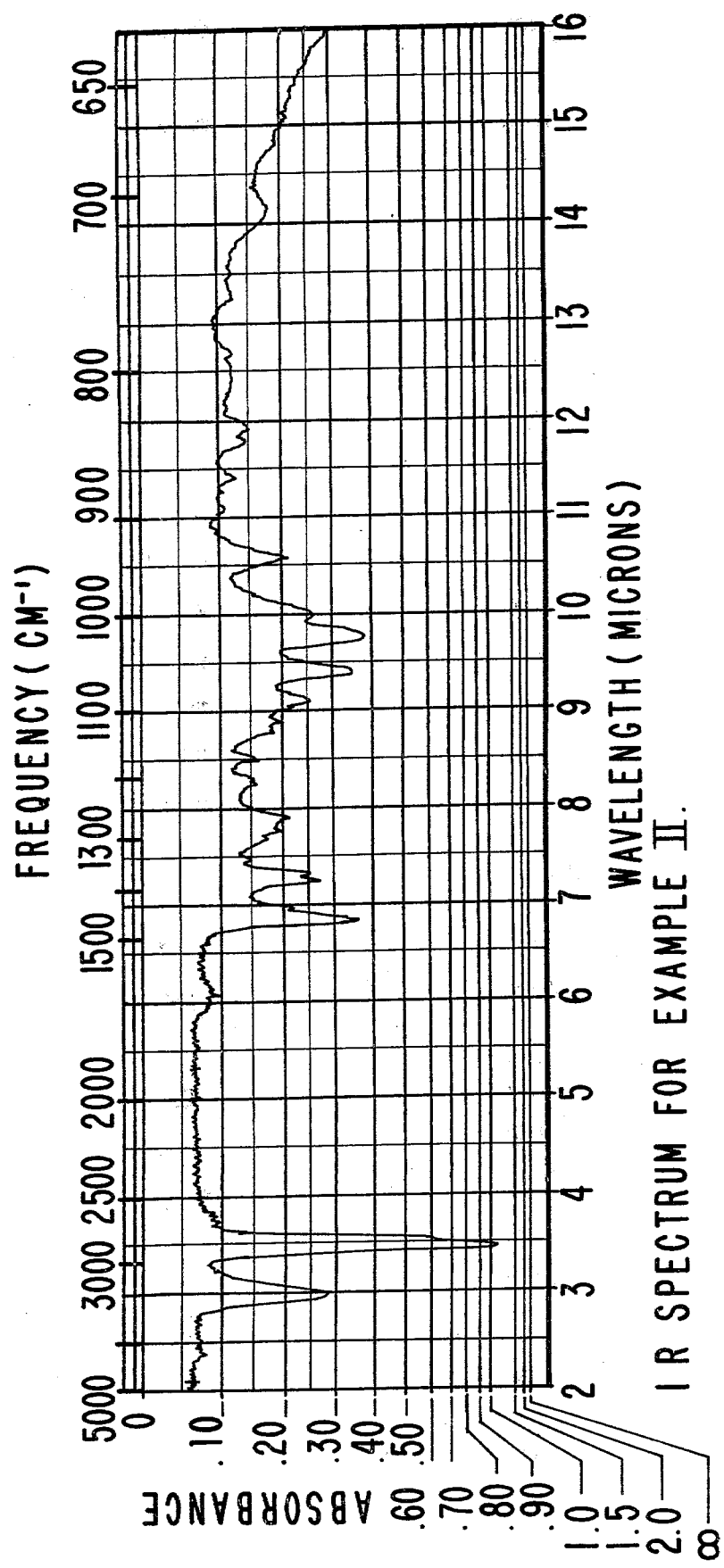

FIG. 4 sets forth the infrared spectrum for the compound having the structure:

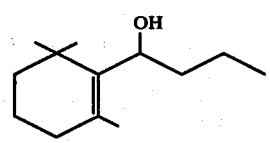

produced according to Example II.

FIG. 5 sets forth the mass spectrum for the compound having the structure:

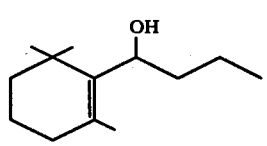

produced according to Example II.

FIG. 6 sets forth the NMR spectrum for the compound having the structure:

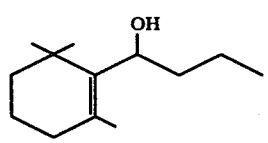

produced according to Example II.

THE INVENTION

The present invention provides an economical, efficient process for synthesizing compounds having the generic structure:

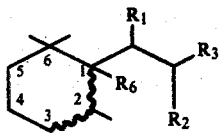

wherein $R_1$ is one of OH, $$\overset{O}{\underset{\|}{}},$$

OMgX or H; $R_2$ is $$\overset{O}{\underset{\|}{}},$$

OH, OMgX, CH$_3$, H; $R_3$ is one of methyl ethyl, 1-propyl or 2-propyl; X is chloro, bromo or iodo; $R_6$ is hydrogen or no moiety; one of the wavy lines is a carbon-carbon double bond and the other of the wavy lines is a carbon-carbon single bond; with the first proviso that when the $\Delta^{2,3}$ bond is a carbon-carbon double bond, then $R_6$ is hydrogen and the moieties $R_6$ and

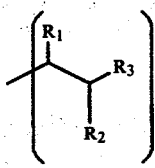

are so juxtaposed as to give rise to two different groups of stereoisomers of the molecular genus:

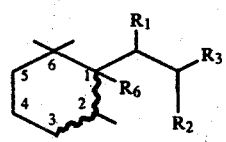

and with the second proviso that when $R_1$ is one of $$\overset{O}{\underset{\|}{}},$$

OH or OMgX then $R_2$ is hydrogen or methyl; and when $R_2$ is one of $$\overset{O}{\underset{\|}{}},$$

OH or OMgX then $R_1$ is hydrogen.

Examples of the structures of compounds represented by the generic structure:

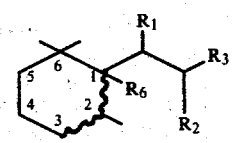

are as follows:

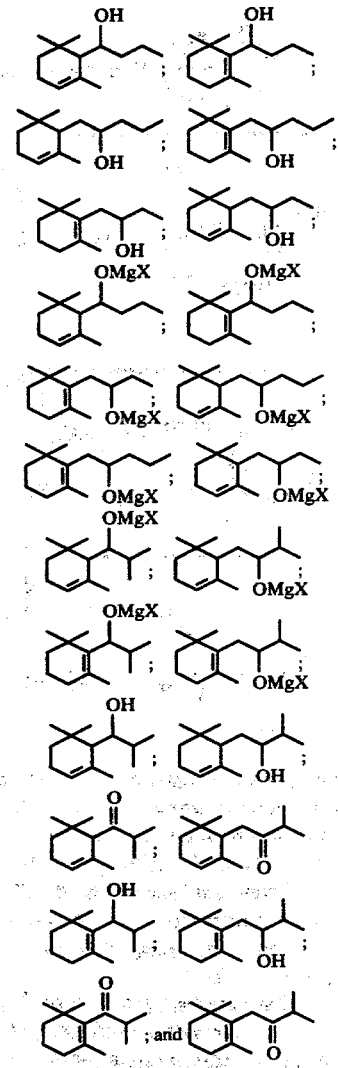

With the exception of the organometalic compounds wherein $R_1$ or $R_2$ is OMgX, the 1-oxyalkyl-2,6,6-trimethylcyclohexene derivatives of our invention as well as mixtures thereof produced according to the process of our invention are capable of augmenting or enhancing camphoraceous, herbaceous, minty, musty/earthy, oriental, floral/oriental, fruity, raspberry-like, sweet, peach-like, woody, damascenone-like and tobacco-like aroma and taste nuances for foodstuff flavors, chewing gum flavors, toothpaste flavors and medicinal product flavors; particularly raspberry flavors, peach flavors, dried fruit flavors, apple flavors, blueberry flavors, nut flavors, peppermint flavors and tobacco flavors.

The 1-oxyalkyl-2,6,6-trimethylcyclohexene derivatives of our invention are produced by, in general, reacting alphacyclocitral, betacyclocitral, alphahomocyclocitral or betahomocyclocitral with a $C_2$ or $C_3$ alkyl Grignard reagent and then hydrolyzing the resulting organometalic compound to form alcohols and either using the resulting alcohols for their own organoleptic properties in foodstuffs or further oxidizing these alcohols to form ketones which are also useful for their organoleptic properties in augmenting or enhancing the aroma or taste of foodstuff flavors. The reaction sequence is set forth in generic form as follows:

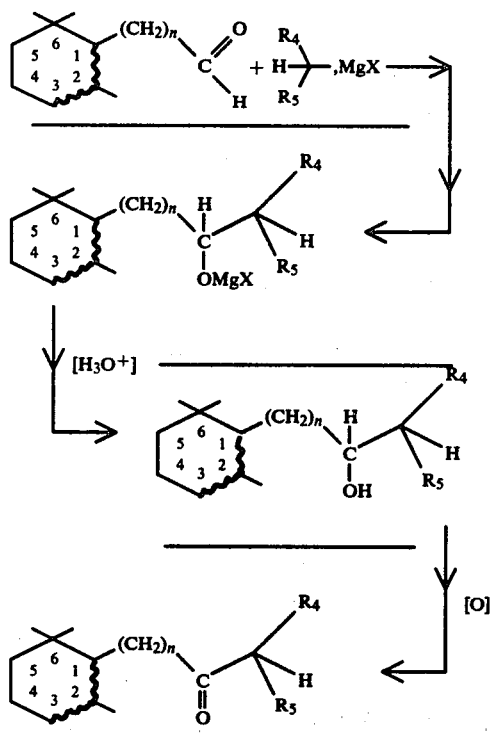

wherein one of the wavy lines is a carbon-carbon double bond and the other of the wavy lines is a carbon-carbon single bond; wherein n is zero or one; wherein X is chloro, bromo or iodo; wherein each of $R_4$ and $R_5$ are the same or different and each represents hydrogen, methyl or ethyl, with the sum, "s", of carbon atoms in $R_4$ and $R_5$, taken together, being governed by the mathematical inequality: $1 \leq S \leq 2$.

More specifically, the first reaction of the process of our invention is between alphacyclocitral, betacyclocitral, alphahomocyclocitral or betahomocyclocitral having the structures:

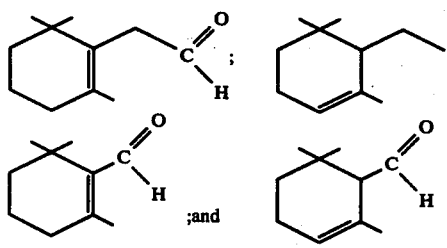

and an alkyl magnesium halide having one of the structures:

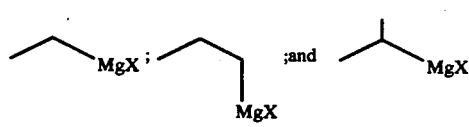

wherein X is chloro, bromo or iodo to form an organometallic compound such as those having one of the structures:

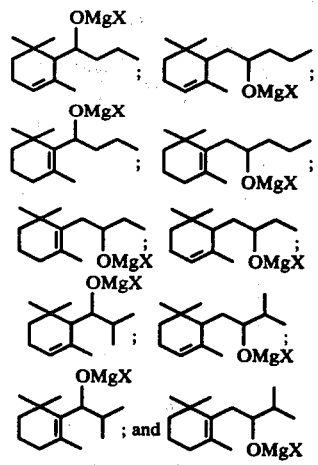

This first reaction takes place in the presence of a solvent which is not reactive with the other reaction ingredients; for example, diethyl ether and tetrahydrofuran. At the termination of this first reaction, the resulting organometallic compound is hydrolyzed with water and, if desired, a small amount of dilute mineral acid such as hydrochloric acid. The hydrolysis of the organometallic compound yields an alcohol such as one of the compounds having a structure:

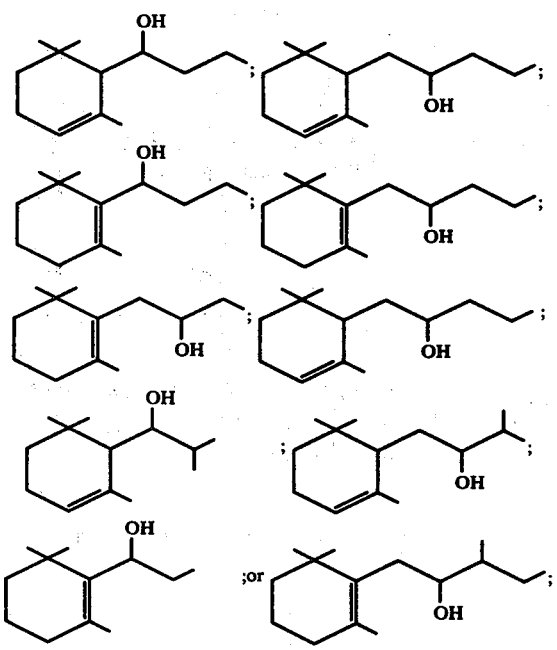

The reaction with the Grignard reagent preferably takes place at the reflux temperature of the solvent; for example when using diethylether the reaction preferably takes place at temperatures of between 30° and 40° C.; more preferably at 35° C. at one atmosphere pressure. The hydrolysis reaction preferably takes place at temperatures of between 0° C. and 20° C.; more preferably between 0° C. and 10° C. At the end of the hydrolysis reaction the resulting product is "worked up" by means of washing with saturated aqueous sodium chloride solution and drying the thus-extracted material with, for example, anhydrous magnesium sulfate. The resulting product is then stripped of solvent and distilled using a fractional distillation column. The resulting distillate may then, if desired, be used "as-is" for its organoleptic properties or it may be further reacted, for example, by oxidation to from the resulting ketone. Suitable oxidizing agents for such a purpose are: potassium dichromate, Jones reagent and oxygen using a suitable catalyst such as copper.

The resulting compounds of our invention are mixtures of stereoisomers in the case of the alcohols and in the case of the ketones wherein the double bond in the cyclohexene ring is at the $\Delta^{2,3}$ position. The mixtures of stereoisomers may be separated according to techniques well known to one having ordinary skill in the art. Thus, for example, the compound having the structure:

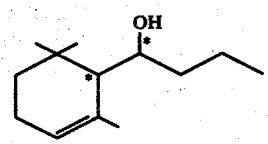

has two asymmetric carbon atoms signified by the carbon atoms which have asterisks (*) adjacent thereto; and the compound having the structure:

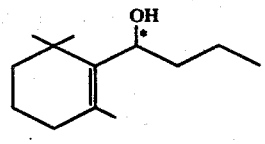

has one asymmetric carbon atom signified by the carbon atom which has an asterisk (*) adjacent thereto. Thus, the compound having the structure:

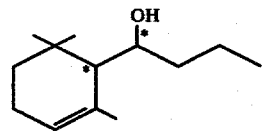

has four stereoisomers, to wit:

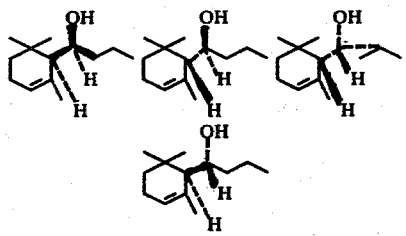

These compounds in order to be separated can be reacted with pure (+) 2-methoxylactic acid having the structure:

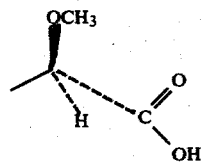

in order to form a (++) lactic acid, for example:

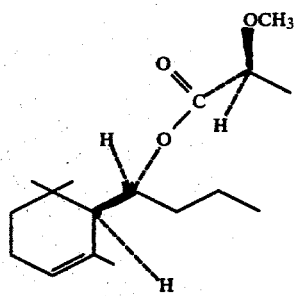

Such esters as the one having the structure:

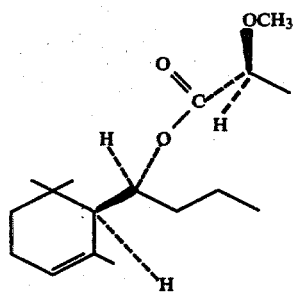

may be separated from the other stereoisomeric esters as by means of column chromatography.

Examples of the products produced according to the process of our invention and their organoleptic properties are as follows:

| Structure of Products | Food Flavor Affecting Properties |
|---|---|
| OH (structure) | A camphoraceous/eucalyptus, herbaceous, minty, musty/earthy, floral/oriental, fruity, raspberry-like, creamy aroma with a camphoraceous/eucalyptus, herbaceous, minty, musty/earthy, floral/oriental, fruity, raspberry, creamy, minty/cooling flavor characteristic at 2ppm. |
| OH (structure) | A sweet, oriental, raspberry-like, peach-like, woody, damascenone-like, tobacco-like aroma with a sweet, oriental-like, raspberry-like, peach-like, woody, damascenone-like, tobacco-like taste at 5ppm. |

When the 1-oxyalkyl-2,6,6-trimethylcyclohexene derivatives of our invention are used as food flavor adjuvants, the nature of the co-ingredients included with the 1-oxyalkyl-2,6,6-trimethylcyclohexene derivatives of our invention used in formulating the product composition will also serve to alter, modify, augment or enhance the organoleptic characteristics of the ultimate foodstuff treated therewith.

As used herein in regard to flavors, the terms "alter," "modify" and "augment" in their various forms mean "supplying or imparting flavor character or note to otherwise bland, relatively tasteless substances or augmenting the existing flavor characteristic where a natural flavor is deficient in some regard or supplementing the existing flavor impression to modify its quality, character or taste."

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, chewing gums, vegetables, cereals, soft drinks, snacks and the like.

As used herein, the term "medicinal product" includes both solids and liquids which are ingestible non-toxic materials which have medicinal value such as cough syrups, cough drops, aspirin and chewable medicinal tablets.

The term "chewing gum" is intended herein to mean a composition which comprises a substantially water-insoluble, chewable plastic gum base such as chickle, or substitutes therefor, including jelutong, guttakay rubber or certain comestible natural or synthetic resins or waxes. Incorporated with the gum base in admixture therewith may be plasticizers or softening agents, e.g., glycerine; and a flavoring composition which incorporates one or more of the alkyl-2,6,6-trimethylcyclohexene derivatives of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxy-anisole (mixture of 2- and 3-tertiary-butyl-4-hydroxy-anisole), butylated hydroxy toluene (2,6-ditertiary-butyl-4-methyl phenol), propyl gallate and the like and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins and emulsifiers, e.g., mono- and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g. carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid and 2-methyl-cis-3-pentenoic acid; ketones and aldehydes, e.g., acetaldehyde, acetophenone, acetone, acetyl methyl carbinol, acrolein, n-butanal, crotonal, diacetyl, 2-methyl butanal, beta,-beta-dimethyl-acrolein, methyl-n-amyl ketone, n-hexanal, 2-hexenal, iso-pentanal, hydrocinnamic aldehyde, cis-3-hexenal, 2-heptenal, n-nonylaldehyde, 4-(p-hydroxyphenyl)-2-butanone, alpha-ionone, beta-ionone, methyl-3-butanone, benzaldehyde, β-damascone, β-damascenone, acetophenone, 2-heptanone, o-hydroxyacetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methyl furfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanal, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpineol hydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl caprylate, ethyl cinnamate, ethyl crotonate, ethyl formate, ethyl isobutyrate, ethyl isovalerate, ethyl laurate, ethyl myristate, ethyl alpha-methyl-butyrate, ethyl propionate, ethyl salicylate, trans-2-hexenyl acetate, hexyl acetate, 2-hexenyl butyrate, n-hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate and terpenyl acetate; hydorcarbons such as dimethyl naphthalene, n-dodecane, methyl diphenyl, methyl naphthalene, myrcene, naphthalene n-octadecane, n-tetradecane, tetramethyl naphthalene, n-tridecane, trimethyl naphthalene, undecane, caryophyllene, 1-phellandrene, p-cymene and 1-alpha-pinene; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine 2-isopropyl-4,5-dimethylpyrazine, 1-methyl-2-ethylpyrazine, tetramethylpyrazine, trimethylpyrazine; essential oils, such as jasmine absolute, cassia oil, cinnamon bark oil, rose absolute, orris absolute, lemon essential oil, Bulgarian rose, yara yara and vanilla; lactones such as delta nonalactone, gamma nonalactone, delta dodecalactone, gamma dodecalactone, sulfides, e.g., methyl sulfide and other materials such as maltol, acetoin and acetals (e.g., 1,1-diethoxyethane, 1,1-dimethoxyethane and dimethoxymethane.).

The specific flavoring adjuvant selected for use may be either solid or liquid depending upon the desired physical form of the ultimate product, i.e., foodstuff, whether simulated or natural, and should, in any event, (i) be organoleptically compatible with the 1-oxyalkyl-2,6,6-trimethylcyclohexene derivatives of our invention by not covering or spoiling the organoleptic properties (aroma and/or taste) thereof; (ii) be non-reactive with the 1-oxyalkyl-2,6,6-trimethylcyclohexene derivatives of our invention and (iii) be capable of providing an environment in which the 1-oxyalkyl-2,6,6-trimethylcyclohexene derivatives of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of the 1-oxyalkyl-2,6,6-trimethylcyclohexene derivatives employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected to be effective, i.e., sufficient to alter, modify or enhance the organoleptic characteristics of the parent composition, whether foodstuff per se, chewing gum per se, medicinal product per se, toothpaste pre se, or flavor composition.

The use of insufficient quantities of 1-oxyalkyl-2,6,6-trimethylcyclohexene derivatives will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 1-oxyalkyl-2,6,6-trimethylcyclohexene derivatives ranging from a small but effective amount, e.g., 0.05 parts per million up to about 300 parts per million based on total composition are suitable. Concentrations in excess of the maximum quantity stated are not normally recommended, since they fail to provide commensurate enhancement of organoleptic properties.

In those instances, wherein 1-oxyalkyl-2,6,6-trimethylcyclohexene derivatives are added to the foodstuff as an integral component of a flavoring composition, it is, of course, essential that the total quantity of flavoring composition employed be sufficient to yield an effective concentration of 1-oxyalkyl-2,2,6,6-trimethylcyclohexene derivatives in the foodstuff product.

Food flavoring compositions prepared in accordance with the present invention preferably contain 1-oxyalkyl-2,6,6-trimethylcyclohexene derivatives in concentrations ranging from about 0.1% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing 1-oxyalkyl-2,6,6-trimethylcyclohexene derivatives with, for example, gum arabic, gum tragacanth, carrageenan and the like, and thereafter spray-drying the resultant mixture whereby to obtain the particulate solid product. Pre-prepared flavor mixes in powder form, e.g., fruit-flavored powder mixes are obtained by mixing the dried solid components e.g., starch, sugar and the like and one or more 1-oxyalkyl-2,6,6-trimethylcyclohexene derivatives in a dry blender until the requisite degree of uniformity is achieved.

It is presently preferred to combine with 1-oxyalkyl-2,6,6-trimethylcyclohexene derivatives of our invention, the following adjuvants:

p-Hydroxybenzyl acetone;
Geraniol;
Cassia Oil;
Acetaldehyde;
Maltol;
Ethyl methyl phenyl glycidate;
Benzyl acetate;
Dimethyl sulfide;
Eugenol
Vanillin;
Caryophyllene;
Methyl cinnamate;
Guaiacol;
Ethyl pelargonate;
Cinnamaldehyde;
Methyl Anthranilate;
5-Methyl furfural;
Isoamyl acetate;
Isobutyl acetate;
Cuminaldehyde;
Alpha ionone;
Cinnamyl formate;
Ethyl butyrate;
Methyl cinnamate;
Acetic acid;
Gamma-undecalactone;
Naphthyl ethyl ether;
Diacetyl;
Furfural;
Ethyl acetate;
Anethole;
2,3-Dimethyl pyrazine;
2-Ethyl-3-methyl pyrazine;
3-Phenyl-4-pentenal;

2-Phenyl-2-hexenal;
2-Phenyl-2-pentenal;
3-Phenyl-4-pentenal diethyl acetal;
Beta-Damascone (1-crotonyl-2,6,6-trimethylcyclohex-1-ene);
Beta-Damascenone (1-crotonyl-2,6,6-trimethylcyclohexa-1,3-diene);
Beta-cyclohomocitral (2,6,6-trimethylcyclohex-1-ene carboxaldehyde);
Isoamyl butyrate;
Cis-3-hexenol-1;
2-Methyl-2-pentenoic acid;
Elemecine (4-allyl-1,2,6-trimethoxybenzene);
Isoelemecine (4-propenyl-1,2,6-trimethoxybenzene); and
2-(4-Hydroxy-4-methylpentyl) norbornadiene.

The following examples serve to illustrate our invention. However, our invention is not intended to be limited thereto but is only intended to be limited insofar as the claims are concerned. All parts and percentages given herein are by weight unless otherwise specified.

EXAMPLE I

PREPARATION OF DIHYDRO-ALPHA-DAMASCOL

Reaction:

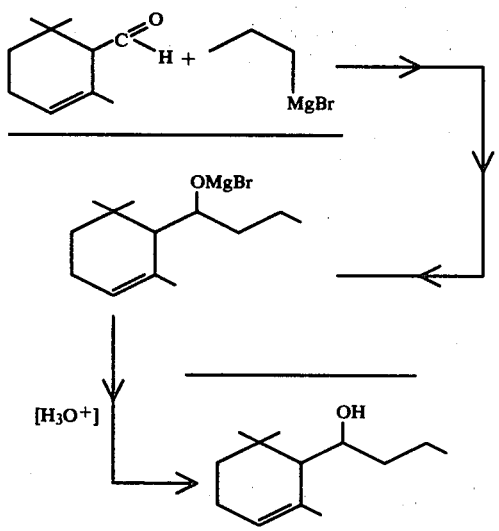

Into a 1 liter reaction flask equipped with magnetic stirrer, nitrogen purge, reflux condenser, thermometer, gas bubbler and heating mantle is placed 9.6 grams of magnesium turnings (0.4 moles) and 100 ml of anhydrous diethyl ether. 43 Grams of 1-bromopropane in 50 ml anhydrous ether is then added dropwise with slight warming until the reaction starts. The rate of addition of the 1-bromopropane is then adjusted whereby reflux is effected in the reaction vessel. Refluxing is continued for a period of one hour after addition of the 1-bromopropane. The reaction mass is then cooled to room temperature and 50 grams of alphacyclocitral in 100 ml diethyl ether is added dropwise to the reaction mass. The reaction mass is allowed to reflux and reflux is continued for one hour after addition. The reaction mass is then cooled to 5° C. and 100 ml of water is added thereto. The hydrolysis reaction is exothermic and the temperature rises and remains at 10°-11° C. for a period of 35 minutes.

The reaction mass is then placed in a one liter separatory funnel. The reaction mass is washed with three 200 ml volumes of saturated sodium chloride solution. The reaction mass is then dried over anhydrous magnesium sulfate and gravity filtered. The solvent is stripped off on a rotary evaporator and the weight of product is 64.2 grams after solvent stripping. The product is then distilled on a micro Vigreux column yielding 52 grams of product. The distillation data is as follows.

| Fraction Number | Vapor Temp.(°C.) | Liquid Temp.(°C.) | Vacuum (mm Hg) | Weight of Fraction (gm.) |
|---|---|---|---|---|
| 1 | 41/45 | 59/60 | 0.073/.07 | 1.2 |
| 2 | 44 | 62 | .05 | 1.2 |
| 3 | 45 | 65 | .04 | 1.8 |
| 4 | 50 | 68 | .036 | 1.8 |
| 5 | 52 | 70 | .036 | 2.2 |
| 6 | 54 | 70 | .036 | 3.0 |
| 7 | 54 | 70 | .036 | 2.9 |
| 8 | 54 | 71 | .036 | 3.0 |
| 9 | 60 | 75 | .036 | 3.2 |
| 10 | 62 | 75 | .036 | 3.1 |
| 11 | 60 | 73 | .034 | 4.7 |
| 12 | 61 | 74 | .034 | 6.1 |
| 13 | 63 | 75 | .034 | 6.9 |
| 14 | 62 | 78 | .03 | 6.4 |
| 15 | 45 | 120 | .03 | 4.5 |

Figure 1:
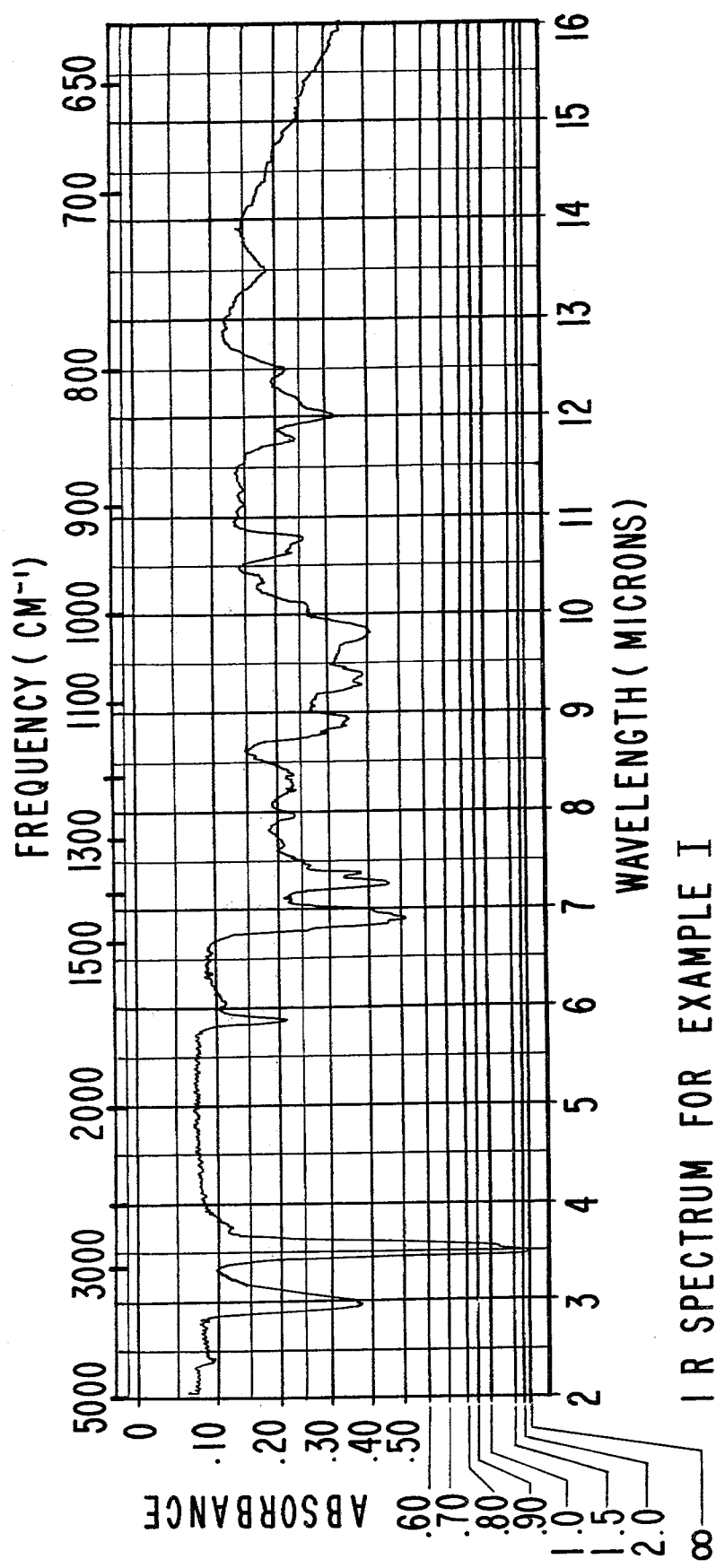
FIG. 1 sets forth the infrared spectrum for the compound produced according to Example I having the structure.

FIG. 1 is the infrared spectrum for the reaction product of this example, having the structure:

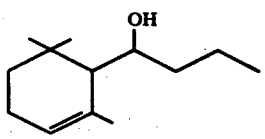

FIG. 2 is the mass spectrum for the reaction product of this example.

FIG. 3 is the NMR spectrum for the reaction product of this example.

EXAMPLE II

PREPARATION OF DIHYDRO-BETA-DAMASCOL

Reaction:

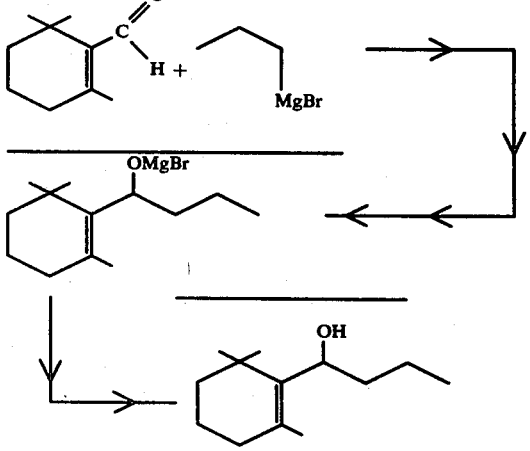

Into a 2 liter reaction flask equipped with mechanical stirrer, nitrogen purge, reflux condenser, thermometer, gas bubbler and heating mantle is placed 19.2 grams of magnesium turnings and 300 ml anhydrous diethyl ether. A mixture of 86 grams of 1-bromopropane in 100 ml anhydrous diethyl ether is then added dropwise with slight warming until the reaction starts; then the rate of addition is adjusted to effect reflux in the reaction mass. Reflux is continued for an additional one hour after the addition of the 1-bromopropane.

100 Grams of betacyclocitral in 200 ml diethyl ether is then added dropwise to the reaction mass at reflux. The reflux temperature is between 35° and 40° C. The refluxing is continued for a period of one hour after the addition of the betacyclocitral. The reaction mass is then cooled to 5° C. and 100 ml water is added thereto while maintaining the reaction mass temperature at 0°-5° C.

The contents of the flask is then transferred to a 2 liter separatory funnel. The reaction mass is washed with three 200 ml portions of saturated sodium chloride. The reaction mass is then dried over anhydrous magnesium sulfate and filtered. The solvent is evaporated on a rotary evaporator yielding 130 grams of dihydrobetadamascol having the structure:

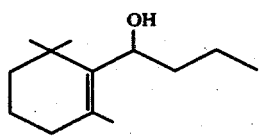

The reaction mass is then distilled on a 5 inch micro column yielding the following distillation data:

| Fraction # | Vapor Temp. (°C.) | Liquid Temp. (°C.) | Vacuum (mm Hg) | Weight of Fraction (gm) |
|---|---|---|---|---|
| 1 | 68/73 | 95/100 | 0.13/0.13 | 6.2 |
| 2 | 80 | 103 | 0.07 | 9.1 |
| 3 | 83 | 104 | 0.07 | 9.5 |
| 4 | 81 | 104 | 0.07 | 7.4 |
| 5 | 82 | 103 | 0.05 | 11.7 |
| 6 | 80 | 100 | 0.04 | 10.9 |
| 7 | 83 | 104 | 0.05 | 7.1 |
| 8 | 80 | 100 | 0.05 | 12.0 |
| 9 | 80 | 100 | 0.05 | 11.4 |
| 10 | 78 | 101 | 0.05 | 14.6 |
| 11 | 64 | 143 | 0.05 | 13.6 |

FIG. 4 is the infrared spectrum for the compound having the structure:

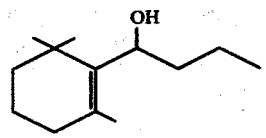

resulting from the distillation.

FIG. 5 is the mass spectrum for the reaction product having the structure:

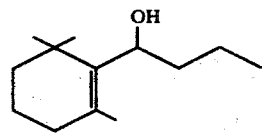

FIG. 6 is the NMR spectrum for the compound having the structure:

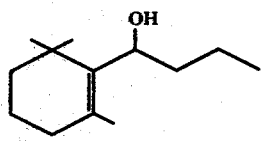

obtained by means of the process of this example.

EXAMPLE III

BASIC RASPBERRY FORMULATION

The following basic raspberry formulation is prepared:

| Ingredients | Parts by Weight |
|---|---|
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic Acid | 10.0 |
| Acetaldehyde | 10.0 |
| Propylene glycol | 930.0 |

To a first portion of this basic formulation, the compound having the structure:

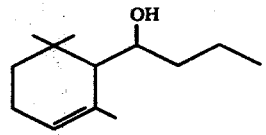

(produced according to Example I) has been added at the rate of 1%. A second portion of this formulation does not contain the compound, alpha-propyl-2,6,6-trimethyl-2-cyclohexene-1-methanol. Both flavors, with and without the compound having the structure:

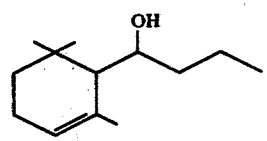

are compared at the rate of 100 ppm in water by a bench panel of experts.

The flavor containing the compound having the structure:

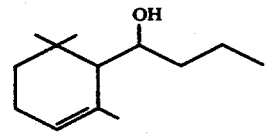

is considered to have a more raspberry kernel, more seedy, herbaceous, more natural character is both aroma and taste. It is therefore preferred as more true to the taste of natural raspberries.

EXAMPLE IV

BASIC RASPBERRY FORMULATION

The following basic raspberry formulation is produced:

| Ingredients | Parts by Weight |
| --- | --- |
| Vanillin | 2.0 |
| Maltol | 5.0 |
| Parahydroxybenzylacetone | 5.0 |
| Alpha-ionone (10% in propylene glycol) | 2.0 |
| Ethyl butyrate | 6.0 |
| Ethyl acetate | 16.0 |
| Dimethyl sulfide | 1.0 |
| Isobutyl acetate | 13.0 |
| Acetic Acid | 10.0 |
| Acetaldehyde | 10.0 |
| Propylene glycol | 930.0 |

To a portion of this basic formulation, the compound having the structure:

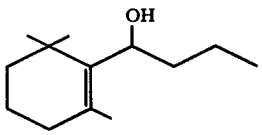

(prepared according to Example II) is added at the rate of 1%. To another portion of this basic formulation nothing is added. Both flavors with and without the compound having the structure:

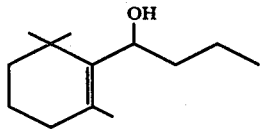

are compared at the rate of 100 ppm in water by a bench panel of experts. The flavor with the compound having the structure:

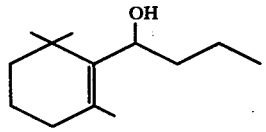

is considered to have a sweeter and more fruity, ripe raspberry character both in aroma and taste. Therefore it is unanimously preferred by the pench panel.

EXAMPLE V

The following mixture is prepared:

| Ingredients | Parts by Weight |
| --- | --- |
| Natural Raspberry Concentrate Juice | 2.5% |
| Water | 85% |
| Sugar syrup (37.5° Baume) | 12.5% |

The ripened raspberry and seedy, raspberry kernel note of this raspberry juice is imparted in increased strength by addition of the compound having the structure:

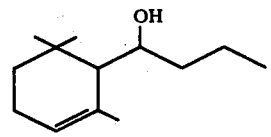

at the rate of from 0.02 parts per million up to 10 parts per million.

EXAMPLE VI

To the raspberry formulation of Example III, the compound having the structure:

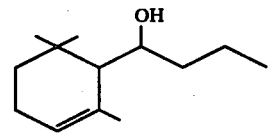

at the rate of 0.2% is added. This material is then called the "test composition". The raspberry formulation without the compound having the structure:

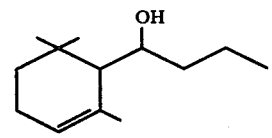

is called the "control composition".

The test and control compositions are added to the food products described hereinafter in the proportions shown for 10 kilograms of material to be flavored:

| Pudding | 5–10 grams (0.15–.1%) |
| --- | --- |
| Cooked sugar | 15–20 grams (.15–2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding—To 500 ml of warmed milk are added with stirring a mixture of 60 grams sucrose and 3 grams of pectin. The mixture is boiled for a few seconds and the flavor is added. The mixture is allowed to cool.

The finished foodstuff samples are tested by a panel of trained persons who express their views about the flavor of the samples. All members of the panel prefer the test samples having a more distinguished ripened raspberry aroma with taste of the ripe raspberries and its seedy kernel note.

EXAMPLE VII

The following mixture is prepared:

| Ingredients | Parts by Weight |
| --- | --- |
| Natural Raspberry Concentrate | 2.5% |
| Juice | 85% |
| Water | |
| Sugar syrup (37.5° Baume) | 12.5% |

The ripened raspberry and seedy, raspberry kernel note of this raspberry juice is imparted in increased strength by addition of the compound having the structure:

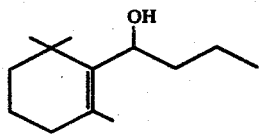

at the rate of from 0.02 parts per million up to 10 parts per million.

EXAMPLE VIII

To the raspberry formulation of Example IV, the compound having the structure:

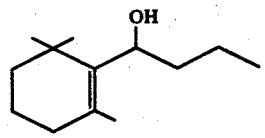

at the rate of 0.2% is added. This material is then called the "test composition". The raspberry formulation without the compound having the structure:

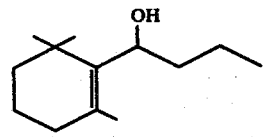

is called the "control composition."

The test and control compositions are added to the food products described hereinafter in the proportions shown for 10 kilograms of material to be flavored:

| Pudding | 5–10 grams (0.15–.1%) |
| Cooked sugar | 15–20 grams (.15–2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding—To 500 ml of warmed milk are added with stirring a mixture of 60 grams sucrose and 3 grams of pectin. The mixture is boiled for a few seconds and the flavor is added. The mixture is allowed to cool.

The finished foodstuff samples are tested by a panel of trained persons who express their views about the flavor of the samples. All members of the panel prefer the test samples having a more distinguished ripened raspberry aroma with taste of the ripe raspberries and its seedy kernel note.

EXAMPLE IX

The following mixture is prepared:

| Ingredients | Parts by Weight |
|---|---|
| Natural Raspberry Concentrate Juice | 2.5% |
| Water | 85% |
| Sugar syrup (37.5° Baume) | 12.5% |

The ripened raspberry and seedy, raspberry kernel note of this raspberry juice is imparted in increased strength by addition of a mixture of 50:50 2-(4-hydroxy-4-methylpentyl)-norbornadiene: compound produced according to Example I having the structure:

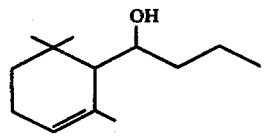

at the rate of from 0.02 parts per million up to 10 parts per million

EXAMPLE X

To the raspberry formulation of Example I, a mixture of 50:50 2-(4-hydroxy-4-methylpentyl)-norbornadiene: compound having the structure:

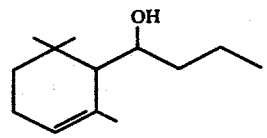

at the rate of 0.2% is added. This material is then called the "test composition". The raspberry formulation without the mixture of 50:50 2-(4-hydroxy-4-methylpentyl)-norbornadiene: compound produced according to Example I having the structure:

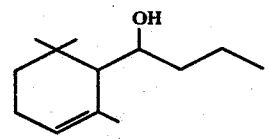

is called the "control composition."

The test and control compositions are added to the food products described hereinafter in the proportions shown for 10 kilograms of material to be flavored:

| Pudding | 5–10 grams (0.15–.1%) |
| Cooked sugar | 15–20 grams (.15–2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding—To 500 ml of warmed milk are added with stirring a mixture of 60 grams sucrose and 3 grams of pectin. The mixture is boiled for a few seconds and the flavor is added. The mixture is allowed to cool.

The finished foodstuff samples are tested by a panel of trained persons who express their views about the flavor of the samples. All members of the panel prefer the test samples having a more distinguished ripened raspberry aroma with taste of the ripe raspberries and its seedy kernel note.

EXAMPLE XI

The following mixture is prepared:

| Ingredients | Parts by Weight |
|---|---|
| Natural Raspberry Concentrate Juice | 2.5% |
| Water | 85% |
| Sugar syrup (37.5° Baume) | 12.5% |

The ripened raspberry and seedy, raspberry kernel note of this raspberry juice is imparted in increased strength by addition of a mixture of 50:50 2-(4-hydroxy-4-methylpentyl)-norbornadiene: compound produced according to Example II having the structure:

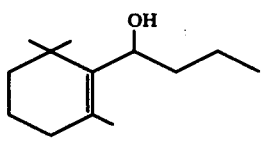

at the rate of from 0.02 parts per million up to 10 parts per million.

EXAMPLE XII

To the raspberry formulation of Example II, a mixture of 50:50 2-(4-hydroxy-4-methylpentyl)-norbornadiene: compound having the structure:

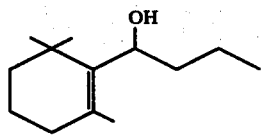

at the rate of 0.2% is added. This material is then called the "test composition". The raspberry formulation without the mixture of 50:50 2-(4-hydroxy-4-methylpentyl)-norbornadiene: compound produced according to Example II having the structure:

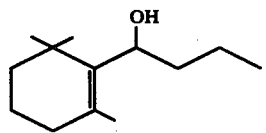

is called the "control composition".

The test and control compositions are added to the food products described hereinafter in the proportions shown for 10 kilograms of material to be flavored:

| Pudding | 5-10 grams (0.15-.1%) |
|---|---|
| Cooked sugar | 15-20 grams (.15-2%) |

Cooked sugar—100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding—To 500 ml of warmed milk are added with stirring a mixture of 60 grams sucrose and 3 grams of pectin. The mixture is boiled for a few seconds and the flavor is added. The mixture is allowed to cool.

The finished foodstuff samples are tested by a panel of trained persons who express their views about the flavor of the samples. All members of the panel prefer the test samples having a more distinguished ripened raspberry aroma with taste of the ripe raspberries and its seedy kernel note.

What is claimed is:

1. A compound defined by the structure:

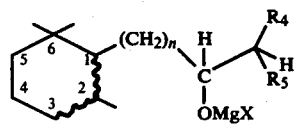

wherein one of the wavy lines is a carbon-carbon single bond and the other of the wavy lines is a carbon-carbon double bond; n is zero or 1; X is selected from the group consisting of chloro, bromo and iodo; $R_4$ and $R_5$ are each the same or different and each is selected from the group consisting of hydrogen, ethyl and methyl, with the proviso that the sum of the carbon atoms in $R_4$ and $R_5$ taken together is greater than or equal to 1 and less than or equal to 2.

2. The compound of claim 1 wherein n is zero and the wavy lines at the $\Delta^{1,2}$ position is a double bond and the wavy line at the $\Delta^{2,3}$ position is a single bond; and $R_4$ is ethyl and $R_5$ is hydrogen.

3. The compound of claim 1 having the structure:

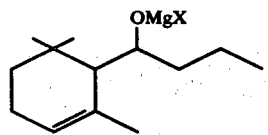

* * * * *